United States Patent [19]

Bartmann et al.

[11] 4,061,766
[45] Dec. 6, 1977

[54] CYCLOPENTANE DERIVATIVES AND PROCESS FOR PREPARING THEM

[75] Inventors: Wilhelm Bartmann, Neuenhain, Taunus; Rudolf Kunstmann, Breckenheim, Taunus; Ulrich Lerch, Hofheim, Taunus; Bernward Schölkens, Kelkheim, Taunus, all of Germany

[73] Assignee: Hoechst Aktiengesellschaft, Frankfurt am Main, Germany

[21] Appl. No.: 736,526

[22] Filed: Oct. 28, 1976

[30] Foreign Application Priority Data

Oct. 31, 1975 Germany .............................. 2548814

[51] Int. Cl.² .................... A61K 31/34; C07C 177/00

[52] U.S. Cl. ...................................... 424/279; 560/53; 560/60; 560/121; 560/122; 542/426; 542/441; 560/14; 260/343.3 P

[58] Field of Search .................... 260/343.3 P, 240 R; 424/279

[56] References Cited

U.S. PATENT DOCUMENTS 3,984,459 10/1976 Babej et al. ...................... 260/468 D Primary Examiner—Natalie Trousoe
Assistant Examiner—Jane T. Fan
Attorney, Agent, or Firm—Curtis, Morris & Safford

[57] ABSTRACT

The present invention relates to cyclopentane derivatives similar to prostaglandins. Due to their antiprostaglandin effect they have valuable properties as medicaments.

4 Claims, No Drawings

CYCLOPENTANE DERIVATIVES AND PROCESS FOR PREPARING THEM

Prostaglandins are a group of natural substances which have been isolated from different animal tissues. In mammals they are responsible for a great number of pharmacological actions among which their effect on the contractions of the unstriped musculature and on the blood pressure may be mentioned. As to further pharmacological properties see i.a. M. F. Cuthbert "The Prostaglandins", Pharmacological and Therapeutic Advances, William Heinemann Medical Books LTD London 1973.

The present invention relates to cyclopentane derivatives similar to the natural prostaglandins and corresponding to the formula I

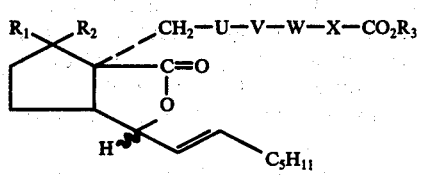

wherein $R_1$ and $R_2$ together represent oxygen or each represents hydrogen or hydroxy, and $R_1$ and $R_2$ are different from each other, $R_3$ is hydrogen, alkyl having 1 to 5 carbon atoms, U is a $(CH_2)_m$-group, m being 0 to 5, a

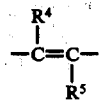

group

group, wherein $R^4$ and $R^5$ are identical or different and represent hydrogen or alkyl having 1 to 5 carbon atoms, V is a single bond, oxygen or a radical of the formulae

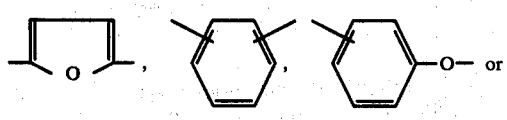 

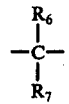

wherein $R_6$ and $R_7$ are identical or different and represent hydrogen or alkyl having 1 to 5 carbon atoms, W is a single bond or a radical of the formula

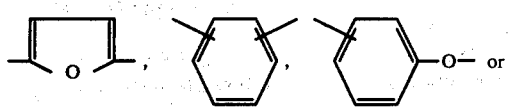

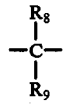

wherein $R_8$ and $R_9$ are identical or different and represent hydrogen or alkyl having 1 to 5 carbon atoms and X is a $(CH_2)_m$-group, wherein m is 0 to 5, as well as the physiologically compatible metal and amine salts of the free acids.

The invention further provides a process for the preparation of the cyclopentane derivatives of the formula I as well as pharmaceutical compositions containing them as active ingredients.

The process comprises reacting a compound of the formula

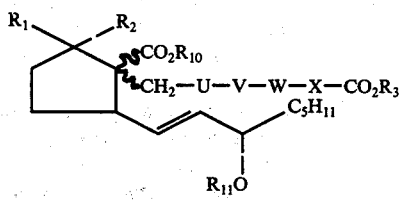

wherein $R_1$, $R_2$, U, V, W, and X have the meaning defined in formula I, $R_3$ and $R_{10}$ are identical or different and represent alkyl having 1 to 5 carbon atoms and $R_{11}$ is hydrogen, cycloalkyl having 5 to 8 carbon atoms, wherein a $CH_2$-group may be substituted by oxygen, $R_{11}$ is an aliphatic or cycloaliphatic acyl radical having 1 to 10 carbon atoms, an aryl, an arylsulfonyl radical, having 6 to 8 carbon atoms or an alkylsulfonyl radical having 1 to 5 carbon atoms, in an aprotic solvent in the presence of catalytic amounts of acids between 15° and 125° C and optionally reducing with sodium borohydride the compound obtained of the formula I, wherein $R_1$ and $R_2$ together represent oxygen.

Among the radicals mentioned for the substituent $R_3$, hydrogen and ethyl are preferred. The substituents $R_4$, $R_5$, $R_6$, $R_7$, $R_8$ and $R_9$ are preferably hydrogen or alkyl having 1 to 3 carbon atoms, in which case the substituents mentioned may be identical or different.

$R_{10}$ is preferably a methyl or ethyl group.

Preferred meanings for $R_{11}$ are: hydrogen, tetrahydropyranyl, alkanoyl having 1 to 5 carbon atoms, especially acetyl, propionyl, butyryl, furthermore cycloaliphatic acyl radicals having 5 cyclic carbon atoms, especially cyclopentylacetyl, cyclopenylethylcarbonyl- and cyclopentylpropylcarbonyl, furthermore phenyl, benzenesulfonyl and p-toluenesulfonyl.

U is preferably a polymethylene chain having up to 3 $CH_2$-groups. X, W and V form together preferably an optionally branched chain having up to 10 members. If V represents a phenylene or phenoxy radical, the remaining molecule portions may be in ortho-, meta- or para-position to one another.

Preferred salts are the alkali metal and alkaline earth metal salts and those which are formed with organic bases such as benzyl amine, morpholine, piperidine, piperazine, especially tris(hydroxymethyl)-aminomethane.

If $R_1$ and $R_2$ are different and represent hydrogen or hydroxy, the compounds of the formula I are stereo isomers. The compounds are furthermore stereo isomers as to the position 1". The double bond of position 2" has generally the trans-form.

Compounds of the formula II are reacted to form compounds of the formula I at a temperature of from 20° to 120° C in an inert atmosphere in aprotic solvents such as acetone, benzene, toluene or dimethylformamide in the presence of organic acids. The compounds of the formula II can be prepared as described in German Offenlegungsschrift No. 2,331,081.

Compounds of the formula I are preferably prepared according to the process of the invention as follows:

Compounds of the formula II are dissolved in absolute acetone or absolute benzene, a catalytic amount of p-toluene-sulfonic acid is added, and the mixture is stirred for 2 to 16 hours at a temperature of from 20° to 60° C. Then the acid is neutralized and the residue is worked up in usual manner. Yields of more than 60 % are obtained.

The compounds of the invention of the formula I are oils which may be used directly of after chromatographic purification, for example on silica gel, or used for further reactions.

The compounds of the invention may be used in the form of their mixtures of isomers; or with the aid of usual separating processes such as thin layer or column chromatography, one or several isomers may be enriched or isolated in pure form.

The following compounds of the formula I may be prepared according to the process of the invention in analogy to the above Example:

1-(6'-Ethoxycarbonylhexyl)-2-(1"-hydroxy-trans-2"-octenyl)5-oxo-cyclopentane-carboxylic acid-γ-lactone from (5RS, 3"SR)-1-(6'-ethoxycarbonylhexyl)-2-oxo-5-[3"-hydroxy-trans-1"-octenyl]-cyclopentane-carboxylic acid ethyl ester 1-(6'-Carboxyhexyl)2-(1"-hydroxy-trans-2"-octenyl)-5-hydroxy-cyclopentane-carboxylic acid-γ-lactone from (5RS, 3"SR)-1-(6'-Carboxyhexyl)-2-hydroxy-5-(3"-hydroxy-trans-1"-octenyl)-cyclopentane-carboxylic acid ethyl ester.

1-(6'-Ethoxycarbonyl-3'-methylhexyl)-2-(1"-hydroxy-trans-2"-octenyl)-5-oxo-cyclopentane-carboxylic acid-γ-lactone from (5RS,3"-SR)-1-(6'-ethoxycarbonyl-3'-methylhexyl)-2-oxo-5-[3"-(2"'-tetrahydropyranyloxy)-trans-1"-oxtenyl]-cyclopentanecarboxylic acid ethyl ester or (5RS,3"SR)-1-(6'-ethoxycarbonyl-3'-methylhexyl)-2-oxo-5-[3"-hydroxy-trans-1"-octenyl]-cyclopentane-carboxylic acid ethyl ester.

1-(6'-Carboxy-3'-methylhexyl)-2-(1"-hydroxy-trans-2"-octenyl)-5-hydroxy-cyclopentane-carboxylic acid-γ-lactone from (5RS,3"SR)-1-(6'-Carboxy-3'-methylhexyl)-2-hydroxy-5-[3"-(2"'-tetrahydropyranyloxy)-trans-1"-octenyl]-cyclopentanecarboxylic acid ethyl ester or (5RS,3"SR)-1-(6'-Carboxy-3'-methylhexyl)-2-hydroxy-5-(3"-hydroxy-trans-1"-octenyl)-cyclopentane-carboxylic acid ethyl ester.

1-(6'-Ethoxycarbonyl-4'-methylhexyl)-2-(1"-hydroxy-trans-2"-octenyl)-5-oxo-cyclopentane-carboxylic acid-γ-lactone from (5RS,3"SR)-1-(6'-Ethoxycarbonyl-4'-methylhexyl)-2-oxo-5-[3"-(2"'-tetrahydropyranyloxy)-trans-1"-octenyl]-cylopentane-carboxylic acid ethyl ester.

1-(6'-Carboxy-4'-methylhexyl)-2-(1"-hydroxy-trans-2"octenyl)-5-hydroxycyclopentane-carboxylic acid-γ-lactone from (5RS,3"-SR)-1-(6'-Carboxy-4'-methylhexyl)-2-hydroxy-5-[3"-(2"'-tetrahydropyranyloxy)-trans-1"-octenyl]-cyclopentane-carboxylic acid ethyl ester.

1-(6'-Ethoxycarbonyl-5'-methylhexyl)-2-(1"-hydroxy-trans-2"-octenyl)-5-oxo-cyclopentane-carboxylic acid-γ-lactone from (5RS,3"SR)-1-(6'-Ethoxycarbonyl-5'-methylhexyl)-2-oxo-5-[3"-(2"'-tetrahydropyranyloxy)-trans-1"-octenyl]-cyclopentane-carboxylic acid ethyl ester.

1-(6'-Carboxy-5'-methylhexyl)-2-(1"-hydroxy-trans-2"-octenyl-5-hydroxy-cyclopentane-carboxylic acid-γ-lactone from (5RS,3"SR)-1-(6'-Carboxy-5'-methylhexyl)-2-hydroxy-5-[3"-(2"'-tetrahydropyranyloxy)-trans-1"-octenyl]-cyclopentanecarboxylic acid ethyl ester.

1-(6'-Ethoxycarbonylheptyl)-2-(1"-hydroxy-trans-2"-octenyl-5-oxo-cyclopentane-carboxylic acid-γ-lactone from (5RS,3"SR)-1-(6'-Ethoxycarbonylheptyl)-2-oxo-5-[3"-(2"'-tetrahydropyranyloxy)-trans-1"-octenyl]-cyclopentane-carboxylic acid ethyl ester.

1(6'-Ethoxycarbonyloctyl)-2-(1"-hydroxy-trans-2"-octenyl)-5-oxo-cyclopentane-carboxylic acid-γ-lactone from:

(5RS,3"SR)-1-(6'-Ethoxycarbonyloctyl)-2-oxo-5-[3"-(2"'-tetrahydropyranyloxy)-trans-1"-octenyl]-cyclopentane-carboxylic acid ethyl ester.

1-(6'-Ethoxycarbonyldecyl)-2-(1"-hydroxy-trans-2"-octenyl)-5-oxo-cyclopentane-carboxylic acid-γ-lactone from (5RS,3"SR)-1-(6'-Ethoxycarbonyldecyl)-2-oxo-5-[3"-(2"'-tetrahydropyranyloxy)-trans-1"-octenyl]-cyclopentane-carboxylic acid ethyl ester.

1-(5'-Ethoxycarbonylhexyl)-2-(1"-hydroxy-trans-2"-octenyl)-5-oxo-cyclopentane-carboxylic acid-γ-lacone from (5RS,3"SR)-1-(5'-Ethoxycarbonylhexyl)-2-oxo-5-[3"-(2"'-tetrahydropyranyloxy)-trans-1"-octenyl]-cyclopentane-carboxylic acid ethyl ester or (5RS,3"SR)-1-(5'-Ethoxycarbonylhexyl)-2-oxo-5[3"-hydroxy-trans-1"-octenyl]-cyclopentane-carboxylic acid ethyl ester.

1-(5'-Ethoxycarbonylheptyl)-2-(1"-hydroxy-trans-2"-octenyl)-5-oxo-cyclopentane-carboxylic acid-γ-lactone from (5RS,3"SR)-1-(5'-Ethoxycarbonylheptyl)-2-oxo-5-[3"-(2"'-tetrahydropyranyloxy)-trans-1"-octenyl]-cyclopentane-carboxylic acid ethyl ester.

1-(5'-Ethoxycarbonylnonyl)-2-(1"-hydroxy-trans-2"-octenyl)-5-oxo-cyclopentane-carboxylic acid-γ-lactone from (5RS, 3"SR)-1-(5'-Ethoxycarbonylnonyl)-2-oxo-5-[3"-(2"'-tetrahydropyranyloxy)-trans-1"-octenyl]-cyclopentanecarboxylic acid ethyl ester or (5RS,3"-SR)-1-(5'-Ethoxycarbonylnonyl)-2-oxo-5-[3"-hydroxy-trans-1"-octenyl]-cyclopentane-carboxylic acid ethyl ester.

1-(4'-Ethoxycarbonylbutyl)-2-(1"-hydroxy-trans-2"-octenyl)-5-oxo-cyclopentane-carboxylic acid-γ-lactone from (5RS,3"SR)-1-(4'-Ethoxycarbonylbutyl)-2-oxo-5-[3"-(2'''-tetrahydropyranyloxy)-trans-1"-octenyl]-cyclopentane-carboxylic acid ethyl ester or (5RS,3"SR)-1-(4'-Ethoxycarbonylbutyl)-2-oxo-5-[3"-hydroxy-trans-1"-oxtenyl]-cyclopentane-carboxylic acid ethyl ester 1-(4'-Ethoxycarbonylpentyl)-2-(1"-hydroxy-trans-2"-octenyl)-5-oxo-cyclopentane-carboxylic acid-γ-lactone from (5RS,3"SR)-1-(4'-Ethoxycarbonylpentyl)-2-oxo-5-[3"-(2'''-tetrahydropyranyloxy)-trans-1"-octenyl]-cyclopentane-carboxylic acid ethyl ester or (5RS,3"SR)-1-(4'-Ethoxycarbonylpentyl)-2-oxo-5-[3"-hydroxy-trans-1"-octenyl]-cyclopentane-carboxylic acid ethyl ester.

1-(3'-Ethoxycarbonyl-trans-2'-propenyl)-2-(1"-hydroxy-trans2"-octenyl)-5-oxo-cyclopentane-carboxylic acid-γ-lactone from (5RS,3"SR)-1-(3'-Ethoxycarbonyl-trans-2'-propenyl)-2-oxo-5-[3"-(2'''-tetrahydropyranyloxy)-trans-1"-octenyl]-cyclopentane-carboxylic acid ethyl ester or (5RS,3"SR)-1-(3'-Ethoxycarbonyl-trans-2'-propenyl)-2-oxo5-[3"-hydroxy-trans-1"-octenyl]-cyclopentane-carboxylic acid ethyl ester.

1-(3'-Ethoxycarbonyl-2'-methylpropyl)-2-(1"-hydroxy-trans-2"-octenyl)-5-oxo-cyclopentane-carboxylic acid-γ-lactone from (5RS,3"-SR)-1-(3'-Ethoxycarbonyl-2'-methylpropyl)-2-oxo-5-[3"-(2'''-tetrahydropyranyloxy)-trans-1"-octenyl]-cyclopentane-carboxylic acid ethyl ester 1-(7'-Ethoxycarbonylheptyl)-2-(1"-hydroxy-trans-2"-octenyl)-5-oxo-cyclopentane-carboxylic acid-γ-lactone from (5RS,3"SR)-1-(7'-Ethoxycarbonylheptyl)-2-oxo-5-[3"-(2'''-tetrahydropyranyloxy)-trans-1"-octenyl]-cyclopentanecarboxylic acid ethyl ester.

1-(6'-Ethoxycarbonyl-4'-oxahexyl)-2-(1"-hydroxy-trans-2"-octenyl)-5-oxo-cyclopentane-carboxylic acid-γ-lactone from (5RS,3"SR)-1-(6'-Ethoxycarbonyl-4'-oxahexyl)-2-oxo-5-[3"-(2'''-tetrahydropyranyloxy)-trans-1"-octenyl]-cyclopentanecarboxylic acid ethyl ester 1-(6'-Ethoxycarbonyl-5'-methyl-4'-oxahexyl)-2-(1"-hydroxy-trans-2"-octenyl)-5-oxo-cyclopentane-carboxylic acid-γ-lactone from (5RS,3"SR)-1-(6'-Ethoxycarbonyl-5'-methyl-4'-oxahexyl)-2-oxo-5-[3"-(2'''-tetrahydropyranyloxy)-trans-1"-octenyl]-cyclopentane-carboxylic acid ethyl ester 1-(6'-Methoxycarbonyl-5'-oxahexyl)-2-(1"-hydroxy-trans-2"-octenyl)-5-oxa-cyclopentane-carboxylic acid-γ-lactone from (5RS,3"SR)-1-(6'-Methoxycarbonyl-5'-oxahexyl)-2-oxo-5-[3"-(2'''-tetrahydropyranyloxy)-trans-1"-octenyl]-cyclopentane-carboxylic acid ethyl ester 1-(6'-Carboxy-5'-oxahexyl)-2-(1"-hydroxy-trans-2"-octenyl)-5-hydroxy-cyclopentane-carboxylic acid-γ-lactone from (5RS,3"SR)-1-(6'-Carboxy-5'-oxahexyl)-2-hydroxy-5-[3"-hydroxy-trans-1"-octenyl]-cyclopentane-carboxylic acid ethyl ester 1-(6'-Ethoxycarbonyl-5'-oxa-cis-2'-hexenyl)-2-(1"-hydroxy-trans-2"-octenyl)-5-oxo-cylopentane-carboxylic acid- lactone from (5RS,3"SR)-1-(6'-Ethoxycarbonyl-5'-oxa-cis-2'-hexenyl)-2-oxo-5-[3"-(2'''-tetrahydropyranyloxy)-trans-1"-octenyl]-cyclopentane-carboxylic acid ethyl ester 1-(6'-Methoxycarbonyl-5'-oxa-trans-2'-hexenyl)-2-(1"-hydroxy-trans-2"-octenyl)-5-hydroxy-cyclopentane-carboxylic acid-γ-lactone from (5RS,3"SR)-1-(6'-Methoxycarbonyl-5'-oxa-trans-2'-hexenyl)-2-oxo-5-[3"-(2'''-tetrahydropyranyloxy)-trans-1"-octenyl]-cyclopentane-carboxylic acid ethyl ester or (5RS,3"SR)-1-(6'-Methoxycarbonyl-5'-oxa-trans-2'-hexenyl)-2-hydroxy-5-[3"-(2'''-tetrahydropyranyloxy)-trans-1"-octenyl]-cyclopentane-carboxylic acid ethyl ester or (5RS,3"SR)-1-(6'-Methoxycarbonyl-5'-oxa-trans-2'-hexenyl)-5-(3"-hydroxy-trans-1"-octenyl)-2-oxo-cyclopentane-carboxylic acid ethyl ester or (5RS,3"SR)-1-(6'-Methoxycarbonyl-5'-oxa-trans-2'-hexenyl)-5-[3"-(3'''-cyclopentylpropylcarbonyloxy)-trans-1"-octenyl]-2-oxocyclopentane-carboxylic acid ethyl ester 1-(6'-Ethoxycarbonyl-5'-oxaheptyl)-2-(1"-hydroxy-trans-2"-octenyl)-5-oxo-cyclopentane-carboxylic acid-γ-lactone from (5RS,3"SR)-1-(6'-Ethoxycarbonyl-5'-oxaheptyl)-2-oxo-5-[3"-(2'''-tetrahydropyranyloxy)-trans-1"-octenyl]-cyclopentane-carboxylic acid ethyl ester.

1-(7'-Methoxycarbonyl-5'-oxa-cis-2'-heptenyl)-2-(1"-hydroxy-trans-2"-octenyl)-5-oxo-cyclopentane-carboxylic acid-γ-lactone from (5RS,3"SR)-1-(7'-Methoxycarbonyl-5'-oxa-cis-2'-heptenyl)-2-oxo-5-[3"-2'''-tetrahydropyranyloxy)-trans-1"-octenyl]-cyclopentane-carboxylic acid ethyl ester 1-[2'-(3"-Ethoxycarbonylpropyl)-benzyl]-2-(1"-hydroxy-trans-2"-octenyl)-5-oxo-cyclopentane-carboxylic acid-γ-lactone from (5RS,3"SR)-1-[2'-(3'''-Ethoxycarbonylpropyl)-benzyl]-2-oxo-5-[3''''-(2'''''-tetrahydropyranyloxy)-trans-1''''-octenyl]-cyclopentane-carboxylic acid ethyl ester 1-[3'-(4"-Ethoxycarbonylphenyl)-propyl]-2-(1"-hydroxy-trans-2"-octenyl)-5-oxo-cyclopentane-carboxylic acid-γ-lactone from (5RS,3"SR)-1-[3'-(4"-Ethoxycarbonylphenyl)-propyl]-2-oxo-5-[3''''-(2'''''-tetrahydropyranyloxy)-trans-1''''-octenyl]-cyclopentane-carboxylic acid ethyl ester 1-(5'-Ethoxycarbonylpentyl)-2-(1"-hydroxy-trans-2"-octenyl)-5-oxo-cyclopentane-carboxylic acid-γ-lactone from (5RS,3"SR)-1-(5'-Ethoxycarbonylpentyl)-2-oxo-5-[3"-(2'''-tetrahydropyranyloxy)-trans-1"-octenyl]-cyclo-pentane-carboxylic acid ethyl ester 1-(3'-Ethoxycarbonyl-2'-methyl-trans-2'-propenyl)-2-(1"-hydroxy-trans-2"-octenyl)-5-oxo-cyclopentane-carboxylic acid-γ-lactone from (5RS,3"SR)-1-(3'-Ethoxycarbonyl-2'-methyl-trans-2'-propenyl)-2-oxo-5-[3"-(2'''-tetrahydropyranyloxy)-trans-1"-octenyl]-cyclopentane-carboxylic acid ethyl ester 1-(6'-Carboxy-5'-oxa-trans-2'-hexenyl)-2-(1"-hydroxy-trans-2"-octenyl)-5-oxo-cyclopentane-carboxylic acid-γ-lactone from (5RS,3"SR)-1-(6'-Carboxy-5'-oxa-trans-2'-hexenyl)-2-hydroxy-5-[3"-(2'''-tetrahydropyranyloxy)-trans-1"-octenyl]-cyclopentane-carboxylic acid ethyl ester or (5RS,3"SR)-1-(6'-Carboxy-5'-oxa-trans-2'-hexenyl)-2-hydroxy-5-(3"-hydroxy-trans-1"-octenyl)-cyclopentane-carboxylic acid ethyl ester 1-(6'-Carboxy-5'-oxa-cis-2'-hexenyl)-2-(1"-hydroxy-trans-2"-octenyl)-5-oxo-cyclopentane-carboxylic acid-γ-lactone from (5RS,3″SR)-1-(6′-Carboxy-5′-oxa-cis-2′-hexenyl)-2-hydroxy-5-[3″-hydroxy-trans-1″-octenyl]-cyclopentane-carboxylic acid ethyl ester 1-(5′-Ethoxycarbonyl-4′-oxapentyl)-2-(1″-hydroxy-trans-2″-octenyl)-5-oxo-cyclopentane-carboxylic acid-γ-lactone from (5RS,3″SR)-1-(5′-Ethoxycarbonyl-4′-oxapentyl)-2-oxo-5-[3″-(2‴-tetrahydropyranyloxy)-trans-1″-octenyl]-cyclopentane-carboxylic acid ethyl ester 1-(4′-Ethoxycarbonyl-3′-oxabutyl)-2-(1″-hydroxy-trans-2″-octenyl)-5-oxo-cyclopentane-carboxylic acid-γ-lactone from (5RS,3″SR)-1-(4′-Ethoxycarbonyl-3′-oxabutyl)-2-oxo-5-[3″-(2‴-tetrahydropyranyloxy)-trans-1″-octenyl]-cyclopentane-carboxylic acid ethyl ester 1-[2′-(3″-Carboxypropyl)-benzyl]-2-(1‴-hydroxy-trans-2‴-octenyl)-5-oxo-cyclopentane-carboxylic acid-γ-lactone from (5RS,3‴SR)-1-[2′-(3″-Carboxypropyl)-benzyl]-2-hydroxy-5-[3‴-(2″″-tetrahydropyranyloxy)-trans-1‴-octenyl]-cyclopentane-carboxylic acid ethyl ester or (5RS,3‴SR)-1-[2′-(3″-Carboxypropyl)-benzyl]-2-hydroxy-5-[3‴-hydroxy-trans-1‴-octenyl]-cyclopentene-carboxylic acid ethyl ester 1-[4′-(2″-Ethoxycarbonylethyl)-benzyl]-2-(1‴-hydroxy-trans-2‴-octenyl)-5-oxo-cyclopentane-carboxylic acid-γ-lactone from (5RS,3‴SR)-1-[4′-(2″-Ethoxycarbonylethyl)-benzyl]-2oxo-5-[3‴-(2″″-tetrahydropyranyloxy)-trans-1‴-octenyl]-cyclo-pentane-carboxylic acid ethyl ester (5RS, 3‴SR)-1-[4′-(2″-Ethoxycarbonylethyl)-benzyl]-2-oxo-5-[3‴-hydroxy-trans-1‴-octenyl]-cyclopentane-carboxylic acid ethyl ester 1-(4′-Ethoxycarbonylbenzyl)-2-(1″-hydroxy-trans-2″-octenyl)-5-oxo-cyclopentane-carboxylic acid-γ-lactone from (5RS,3″SR)-1-(4′-Ethoxycarbonylbenzyl)-2-oxo-5-[3″-(2‴-tetrahydropyranyloxy)-trans-1″-octenyl]-cyclopentane-carboxylic acid ethyl ester or (5RS,3″SR)-1-(4′-Ethoxycarbonylbenzyl)-2-oxo-5-[3″-hydroxy-trans-1″octenyl]-cyclopentane-carboxylic acid ethyl ester 1-[2′-(4″-Ethoxycarbonylphenoxy)-ethyl]-2-(1‴-hydroxy-trans-2‴-octenyl)-5-oxo-cyclopentane-carboxylic acid-γ-lactone from (5RS,3‴-SR)-1-[2′-(4″-Ethoxycarbonylphenoxy)-ethyl]-2-oxo-5-[3‴-(2″″-tetrahydropyranyloxy)-trans-1‴-octenyl]-cyclopentane-carboxylic acid ethyl ester 1-(5′-Ethoxycarbonylfurfuryl)-2-(1″-hydroxy-trans-2″-octenyl)-5-oxo-cyclopentane-carboxylic acid-γ-lactone from (5RS,3″SR)-1-(5′-Ethoxxycarbonylfurfuryl)-2-oxo-5-[3″-(2‴-tetrahydropyranyloxy)-trans-1″-octenyl]-cyclopentane-carboxylic acid ethyl ester Surprisingly, the compounds of the formula I which are closely related to the natural prostaglandins with regard to their structure, as has been mentioned above, have an antiprostaglandin effect. If, for example, a solution of the compounds of the invention in water is added to the isolated guinea pig ileum and, for example, prostaglandin $E_2$ or $F_{2\alpha}$ is added to this solution in concentrations by which the isolated ileum or the isolted uterus are normally stimulated to heavy contractions, only a slight spasmogenic effect or no effect of the prostaglandins $E_2$ and $F_{2\alpha}$ can be detected, according to the concentrations used.

Prostaglandin antagonists which are closely related to the natural prostaglandins as to their structure have only been described by J. Fried in "Prostaglandins", Annals of the New York Academy of Sciences, volume 180, April 1971. But the compounds of the invention are very different from the compounds described as to their structure.

Certain diseases may be attributed to an increased level of natural prostaglandins. Prostaglandins play a part in flammable painful and feverish processes (for example J. R. Vane "Inhibition of Prostaglandin Biosynthesis as the Mechanism of Action of Aspirinlike Drugs" in "Advance in the Bioscience" 9, International Conference on Prostaglandins, Pergamon Press Vieweg, 1973). Furthermore, the pathological spasm caused by prostaglandins, of the unstriped musculature, may cause for example disturbances of the gastric and intestinal motility and circulatory diseases (cf. for example E. W. Horton et al., Lancet I, page 648, (1969) and Nakanoj, Proc.Soc.Ex.Biol.Med., 127, page 1160 (1968)).

Prostaglandins are also involved in the regulation of the reproductive processes of mammals (cf. for example J. A. Mc Cracken, et al., Nature New Biology, 238, page 129 (1972)). Thus, the compounds may be used as medicaments due to their antiprostaglandin effect. Particularly, the inhibition or suppression of the spasmogenic effect on certain unstriped muscles is very desired.

The compounds of the invention of the formula I may be administered in the form of their aqueous solutions or suspensions or as solutions in pharmacologically tolerable organic solvents, as for example in mono- or polyhydric alcohols, dimethylsulfoxide or dimethylformamide, also in the presence of pharmacologically tolerable polymer carriers, for example polyvinyl pyrrolidone. Besides the usual galenic infusion or injection solutions, tablets are also used. Preparations to be applied locally, such as cremes, emulsions, suppositories or aerosols, are prepared.

The compounds of the invention may be used individually or together with other pharmacologically active substances, as, for example, prostaglandin sythetase inhibitors such as the sodium salt of acetyl-salicylic acid.

The following Examples illustrate the invention.

EXAMPLE 1

1-(6′-Ethoxycarbonylhexyl)-2-(1″-hydroxy-trans-2″-octenyl)-5-oxo-cyclopentane-carboxylic acid-γ-lactone 300 mg of (5 RS, 3″SR)-1-(6′-ethoxycarbonylhexyl)-2-oxo-5-[3″-(2‴-tetrahydropyranyloxy)-trans-1″-octenyl]-cyclopentanecarboxylic acid ethyl ester prepared according to German Offenlegungsschrift No. 2,331,081 are heated to boiling in 10 ml of acetone with 10 mg of p-toluene-sulfonic acid for six hours under nitrogen, and the mixture is allowed to stand for 14 hours at room temperature. The acetone is distilled off in vacuo, the residue is taken up in diethyl ether, washed with water, the ether is dried over $Na_2SO_4$ and distilled off in vacuo.

The oily residue is chromatographed on silica gel, and by fractionated elution with cyclohexane/ethyl acetate mixtures in the ratio of 8:2 a by-fraction is obtained which contains the 1-(6′-ethoxycarbonylhexyl)-2-oxo-5-(octa-1,3-dien-1-yl)-cyclopentane-carboxylic acid ethyl ester as determined by the IR and NMR spectra.

| NMR | |
|---|---|
| 5.4–6.4 (4H, m, 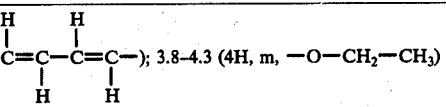); 3.8–4.3 (4H, m, —O—CH$_2$—CH$_3$) | |
| IR: 1720 cm$^{-1}$ | |

Then 150 mg of the main fraction having the following physical data are eluted:

| NMR: | |
|---|---|
| 5.5–6.1 (2H, m, 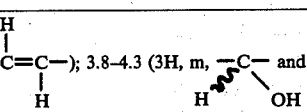); 3.8–4.3 (3H, m, —C— and | |
| —OCH$_2$—CH$_3$) | |
| IR: 1720 and 1775$^{-1}$ | |

By a careful repeated chromatography on silica gel this fraction has been decomposed into two fractions, the IR and NMR data of which were identical to those given above, and which were different only as to the position of a proton.

The isomer isolated first from the column is termed as isomer A.

NMR: as above and additionally 4.7 – 5.0 ppm, 1H, multiplet,

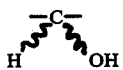

The slowly migrating isomer is called isomer B.

NMR: as above and additionally = 4.2 – 4.5 ppm, 1H, multiplet,

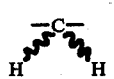

Both isomers are configuration isomers with regard to the position 1″.

EXAMPLE 2

Analogous results are obtained if 300 mg of (5 RS, 3 SR)-1-(6′-ethoxycarbonylhexyl)-2-oxo-5-(3″-hydroxy-trans-1″-octenyl)cyclopentane-carboxylic acid ethyl ester are heated for 3 hours to 50° C in 30 ml of absolute benzene and allowed to stand for 14 hours at room temperature and subsequently worked up as described under Example 1.

EXAMPLE 3

1-(6′-Ethoxycarbonyl-3′-methylhexyl)-2-(1″-hydroxy-trans-2″-octenyl)-5-oxo-cyclopentane-carboxylic acid-γ-lactone 300 mg of (5 RS, 3 SR)-1-(6′-ethoxycarbonyl-3′-methylhexyl)-2-oxo-5-[3″-hydroxy-trans-1″-octenyl)-cyclopentane-carboxylic acid ethyl ester, prepared according to German Offenlegungsschrift No. 2,391,081, are stirred with 30 mg of p-toluenesulfonic acid for 2 ½ hours at 350° C and for 16 hours at room temperature; the whole is mixed with 0.3 ml of triethylamine and the solvent is evaporated in vacuo. The oily residue is taken up in diethyl ether, washed with water, dried, the solvent is evaporated and the oily residue is chromatographed on silica gel. Elution takes place with mixtures of cyclohexane ethyl acetate/glacial acetic acid in the ratio of 60:40:1, and 61 mg of a faster migrating and 130 mg of a more slowly migrating isomer are obtained.

The IR spectra of both isomers are practically identical (1720$^{-1}$ and 1775 cm$^{-1}$).

The NMR spectra of both isomers are practically identical with regard to the position of the olefinic protons and ester protons 5.3–6.1; m, 2 C=C—; 3.8–4.3; m, 2H, —O—CH$_2$—CH$_3$)

and are distinguished from one another as to the position of a multiplet for one proton, the centers of which are = 4.5 – 5.

They are configuration isomers with regard to the position 1″.

What is claimed is:

1. A compound of the formula

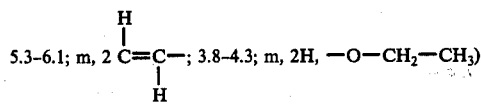

and the physiologically tolerable metal and amine salts thereof, wherein
R$_1$ and R$_2$, taken together, are oxygen;
R$_1$ and R$_2$, taken separately, are each hydrogen or hydroxy but R$_1$ and R$_2$ are different;
R$_3$ is hydrogen or alkyl having 1 to 5 carbon atoms;
U is —(CH$_2$)$_m$—, where
$m$ is 0 to 5, or is

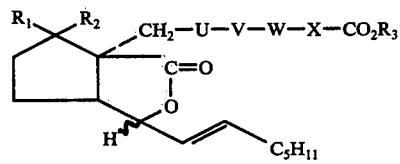

where R$_4$ and R$_5$ are the same or different and are hydrogen or alkyl having 1 to 5 carbon atoms;
V is a single bond, oxygen,

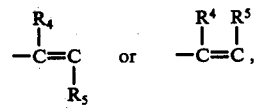

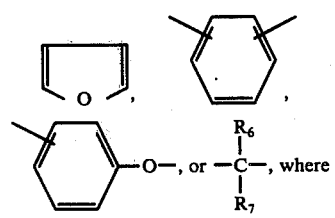

R$_6$ and R$_7$ are the same or different and are hydrogen or alkyl having 1 to 5 carbon atoms;
W is a single bond or

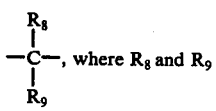

where $R_8$ and $R_9$ are the same or different and are hydrogen or alkyl having 1 to 5 carbon atoms; and X is $-(CH_2)_m-$, where $m$ is 0 to 5.

2. A process for the preparation of compound as in claim 1 which comprises heating a compound of the following formula

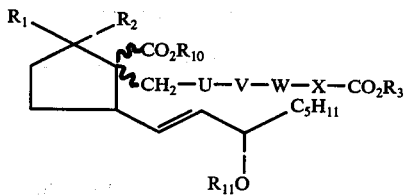

wherein $R_1$, $R_2$, U, V, W and X have the meanings set forth in claim 6, $R_3$ and $R_{10}$ are identical or different and represent alkyl having 1 to 5 carbon atoms and $R_{11}$ is hydrogen, cycloalkyl having 5 to 8 carbon atoms, tetrahydropyranyl, aliphatic or cycloaliphatic carboxy acyl having up to 10 carbon atoms, alkylsulfonyl having 1 to 5 carbon atoms or aryl or arylsulfonyl each having 6 to 8 carbon atoms, in an aprotic solvent in the presence of a catalytic amount of an acid between 15° and 125° C and optionally reducing with sodium borohydride the compound obtained when $R_1$ and $R_2$ together represent oxygen.

3. A pharmaceutical composition useful as a prostaglandin antagonist, said composition comprising a pharmaceutically acceptable carrier and, as the active ingredient, a compound or salt as in claim 1 in an amount producing an antiprostaglandin effect.

4. A method for antagonizing the effects of prostaglandins, which method comprises administering a compound as in claim 1 in an amount producing an antiprostaglandin effect.

* * * * *